US007138441B1

(12) United States Patent
Zhang

(10) Patent No.: US 7,138,441 B1
(45) Date of Patent: Nov. 21, 2006

(54) BIOABSORBABLE BLENDS AND SURGICAL ARTICLES THEREFROM

(75) Inventor: Guanghui Zhang, Belle Mead, NJ (US)

(73) Assignee: United States Surgical Corporation, North Haven, CT (US)

( * ) Notice: Subject to any disclaimer, the term of this patent is extended or adjusted under 35 U.S.C. 154(b) by 0 days.

(21) Appl. No.: 09/580,884

(22) Filed: May 30, 2000

Related U.S. Application Data

(60) Provisional application No. 60/136,731, filed on May 28, 1999.

(51) Int. Cl.
C08L 67/00 (2006.01)
C08G 63/08 (2006.01)
A61L 24/00 (2006.01)

(52) U.S. Cl. ........................ 523/113; 523/122; 525/419; 528/354

(58) Field of Classification Search ............... 524/206; 523/113, 118, 122; 525/419; 528/354
See application file for complete search history.

(56) References Cited

U.S. PATENT DOCUMENTS

| | | | |
|---|---|---|---|
| 3,223,083 A | 12/1965 | Cobey | 128/92 |
| 3,360,124 A | 12/1967 | Stonehill | 206/84 |
| 3,523,628 A | 8/1970 | Colvin et al. | 222/107 |
| 3,524,537 A | 8/1970 | Winter | 206/47 |
| 3,527,841 A | 9/1970 | Wicker et al. | 260/823 |
| 3,559,652 A | 2/1971 | Banitt et al. | 128/334 |
| 3,564,078 A | 2/1971 | Wicker et al. | 260/881 |
| 3,667,472 A | 6/1972 | Halpern | 128/334 R |
| 3,699,076 A | 10/1972 | Thomsen et al. | 260/41 |
| 3,722,599 A | 3/1973 | Robertson et al. | 128/334 |
| 3,961,966 A | 6/1976 | Brinkmann et al. | 106/36 |
| 3,975,422 A | 8/1976 | Buck | 260/465.4 |
| 3,995,641 A | 12/1976 | Kronenthal et al. | 128/335 |
| 4,009,044 A | 2/1977 | Korshak et al. | 106/287 R |
| 4,012,402 A | 3/1977 | Buck | 260/448.2 |
| 4,035,334 A | 7/1977 | Davydov et al. | 260/42.21 |
| 4,041,061 A | 8/1977 | Buck | 260/464 |
| 4,041,062 A | 8/1977 | Buck | 260/465 D |
| 4,041,063 A | 8/1977 | Buck | 260/465.4 |
| 4,086,266 A | 4/1978 | Corey | 260/465.4 |
| 4,138,040 A | 2/1979 | Stock | 222/420 |
| 4,192,021 A | 3/1980 | Deibig et al. | 3/1.9 |
| 4,313,865 A | 2/1982 | Teramoto et al. | 260/31.4 R |
| 4,359,454 A | 11/1982 | Hoffman | 424/5 |
| 4,408,699 A | 10/1983 | Stock | 222/149 |
| 4,413,753 A | 11/1983 | Stock | 222/149 |
| 4,444,933 A | 4/1984 | Columbus et al. | 524/292 |
| 4,498,609 A | 2/1985 | Stock | 222/420 |
| 4,704,466 A | 11/1987 | Engel et al. | 558/411 |
| 4,740,534 A | 4/1988 | Matsuda et al. | 523/111 |
| 4,804,691 A | 2/1989 | English et al. | 523/118 |
| 4,876,323 A | 10/1989 | Engel et al. | 526/310 |
| 4,935,261 A | 6/1990 | Srivastava et al. | 427/10 |
| 4,958,748 A | 9/1990 | Otake | 222/131 |
| 4,963,666 A | 10/1990 | Lalson | 536/55.1 |
| 4,981,483 A | 1/1991 | Akimova et al. | 606/214 |
| 5,154,320 A | 10/1992 | Bolduc | 222/145 |
| 5,254,132 A | 10/1993 | Barley et al. | 606/214 |
| 5,259,835 A | 11/1993 | Clark et al. | 602/48 |
| 5,268,436 A | 12/1993 | Huver et al. | 526/216 |
| 5,292,333 A | 3/1994 | Johnson | 606/214 |
| 5,292,362 A | 3/1994 | Bass et al. | 106/124 |
| 5,306,490 A | 4/1994 | Barley, Jr. | 424/78.35 |
| 5,328,687 A | 7/1994 | Leung et al. | 424/78.35 |
| 5,340,873 A | 8/1994 | Mitry | 525/10 |
| 5,347,044 A | 9/1994 | Byerley et al. | 560/355 |
| 5,350,798 A | 9/1994 | Linden et al. | 525/41 |
| 5,383,925 A | 1/1995 | Schmitt | 623/1 |
| 5,393,826 A | 2/1995 | Huver et al. | 524/722 |
| 5,403,591 A | 4/1995 | Tighe et al. | 424/445 |
| 5,428,115 A | 6/1995 | Huver et al. | 525/379 |
| 5,443,454 A | 8/1995 | Tanabe et al. | 604/264 |
| 5,445,597 A | 8/1995 | Clark et al. | 602/48 |
| 5,480,064 A | 1/1996 | Yan | 222/83 |
| 5,480,935 A | 1/1996 | Greff et al. | 524/776 |
| 5,501,370 A | 3/1996 | Okamura et al. | 222/111 |
| 5,514,371 A | 5/1996 | Leung et al. | 424/78.35 |
| 5,514,372 A | 5/1996 | Leung et al. | 424/78.35 |
| 5,527,353 A | 6/1996 | Schmitt | |
| 5,530,037 A | 6/1996 | McDonnell et al. | 522/79 |
| 5,536,799 A | 7/1996 | Takahashi | 526/298 |
| 5,543,218 A * | 8/1996 | Bennett et al. | 428/375 |
| 5,550,172 A * | 8/1996 | Regula et al. | 523/118 |
| 5,554,365 A | 9/1996 | Byram et al. | 424/78.02 |
| 5,575,997 A | 11/1996 | Leung et al. | 424/78.35 |
| 5,580,565 A | 12/1996 | Tighe et al. | 424/400 |
| 5,582,834 A | 12/1996 | Leung et al. | 424/426 |
| 5,624,669 A | 4/1997 | Leung et al. | 424/78.35 |
| 5,653,769 A | 8/1997 | Barley et al. | 623/66 |

(Continued)

FOREIGN PATENT DOCUMENTS

GB  2306469  6/1997

OTHER PUBLICATIONS

"A randomized trial comparing octylcyanoacrylate tissue adhesive and sutures in the management of lacerations.", Journ.Amer.Med. Ass., 277:1527-1530, (1997).

(Continued)

Primary Examiner—Tae H. Yoon

(57) ABSTRACT

Blends made of bioabsorbable materials including glycolide, lactide, caprolactone, dioxanone, trimethylene carbonate, alkylene glycols, esteramides, etc., and polymers and copolymers thereof with cyanoacrylates are described. Processes for making the polymers and surgical articles made totally or in part from such polymers, including sutures, are also described.

8 Claims, No Drawings

U.S. PATENT DOCUMENTS

| | | | |
|---|---|---|---|
| 5,665,817 A | 9/1997 | Greff et al. | 524/776 |
| 5,684,042 A | 11/1997 | Greff et al. | 514/527 |
| 5,716,607 A | 2/1998 | Byram et al. | 424/78.02 |
| 5,716,608 A | 2/1998 | Byram et al. | 424/78.02 |
| 5,720,994 A | 2/1998 | Asai | 425/556 |
| 5,730,994 A | 3/1998 | Askill et al. | 424/402 |
| 5,739,205 A | 4/1998 | Nishino et al. | 524/555 |
| 5,753,699 A | 5/1998 | Greff et al. | 514/527 |
| 5,922,357 A | 7/1999 | Coombes et al. | |
| 5,962,427 A * | 10/1999 | Goldstein et al. | 514/44 |
| 6,020,004 A | 2/2000 | Shah | |
| 6,103,778 A * | 8/2000 | Hyon et al. | 523/111 |
| 6,299,631 B1 * | 10/2001 | Shalaby | 606/214 |

OTHER PUBLICATIONS

International Search Report, Aug. 8, 2000.

\* cited by examiner

BIOABSORBABLE BLENDS AND SURGICAL ARTICLES THEREFROM

This application claims the benefit of U.S. Provisional Patent Application 60/136,731 filed May 28, 1999.

TECHNICAL FIELD

Bioabsorbable blends of materials including glycolide, lactide, caprolactone, dioxanone, trimethylene carbonate, alkylene glycols, esteramides, etc., and polymers and copolymers thereof with cyanoacrylates are described. Processes for making the polymers and surgical articles made totally or in part from such polymers, including sutures, are also described.

BACKGROUND OF THE INVENTION

Cyanoacrylate based tissue adhesives are well known in the art for use in wound closure. It is thought that such adhesives can be applied without the use of a local anesthetic and without the trauma caused by a needle and suture. However, commercially available products such as Dermabond, commercially available from Closure Medical, Raleigh, N.C., and Indermill, commercially available from Davis & Geck, are not bioabsorbable and hence are not suitable for internal applications.

Therefore, it would be advantageous to provide a bioabsorbable tissue adhesive. Such tissue adhesives would not only be of use in external applications, but also could be used in more invasive procedures such as abdominal or cardiothoracic surgery.

SUMMARY OF THE INVENTION

It has now surprisingly been found that a cyanoacrylate and a bioabsorbable component derived from glycolide, lactide, caprolactone, dioxanone, trimethylene carbonate, alkylene glycols, esteramides, etc., and polymers and copolymers thereof, can be blended together to form a material that is bioabsorbable and provides excellent flexibilty and adhesive properties, while maintaining acceptable viscosity and curing times when applied to mammalian tissues.

In one embodiment blends used in forming such a tissue adhesive are prepared by blending about 5 to about 60 percent by weight of a bioabsorbable component with about 95 to about 40 percent by weight of a cyanoacrylate.

DESCRIPTION OF THE PREFERRED EMBODIMENTS

The bioabsorbable blend may be prepared by conventional methods well known in the art. Suitable blends can be prepared by blending about 5 to about 60 percent by weight of a bioabsorbable component with about 95 to about 40 percent by weight of a cyanoacrylate. Preferrably the blend may include about 10 to about 40 percent by weight of a bioabsorbable component and about 90 to about 60 percent by weight of a cyanoacrylate. In one embodiment the blend may include about 12 to about 20 percent by weight of a bioabsorbable component and about 88 to about 80 weight percent of a cyanoacrylate. It is to be understood that as used herein the term "bioabsorbable component" shall not imply that the cyanoacrylate component is or is not bioabsorbable.

Suitable cyanoacrylates include branched or straight chain $C_4$–$C_{12}$ cyanoacrylates, such as butyl cyanoacrylates (such as n-butyl cyanoacrylate, perfluoro butyl cyanoacrylate, and tert-butyl cyanoacrylate), pentyl cyanoacrylate, hexyl cyanoacrylate, octyl cyanocarylates (such as n-octyl cyanoacrylate and 2-octyl cyanoacrylate); straight or branched chain alkyloxyalkyl cyanoacrylates; straight or branched chain cyanoacrylates having multiple ether or ester linkages therein; and ethylenically unsaturated cyanoacrylates with functional groups such as cyclic alkanes.

Suitable bioabsorbable materials include glycolide, lactide, caprolactone, dioxanone, trimethylene carbonate, alkylene glycols, esteramides, etc., and blends, polymers and copolymers thereof. Suitable bioabsorbable copolymers include both linear and star shaped copolymers derived from epsilon-caprolactone and glycolide, lactide, dioxanone, and/or trimethylene carbonate initiated with an alchohol such as dodecanol, a diol such as diethylene glycol, or a polyol such as glycerol, pentaerythritol, or mannitol, such as those disclosed in U.S. Pat. No. 5,543,218. A "predominant amount" as defined herein is an amount greater than about 50 weight percent.

Suitable caprolactone containing polymers for use in the bioabsorbable component of the blend described herein include copolymers which can be synthesized by well known techniques; see, for example Principles of Polymerization, George Odian, III Edition; 1991 pp. 569–573, the contents of which are incorporated herein by reference. Suitable caprolactone containing copolymers can be obtained by polymerizing a major amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

Suitable monomers which can be copolymerized with epsilon-caprolactone include glycolide, lactide, p-dioxanone and trimethylene carbonate.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like. The polyhydric alcohol initiator is generally employed in small amounts, e.g., from about 0.5 to about 5, and preferably from about 0.1 to about 2, weight percent of the total monomer mixture.

The copolymer for use in the bioabsorbable component of the blend described herein can contain from about 70 to about 98, and preferably from about 80 to about 95, weight percent epsilon-caprolactone-derived units, the balance of the copolymer being derived from the other copolymerizable monomer(s). The inherent viscosity of the copolymer generally ranges from about 0.10 to about 0.60, and preferably from about 0.20 to about 0.50, dl/g when measured in chloroform at a concentration of 0.2500 g/dl at 30° C.

The bioabsorbable component may then be blended with the cyanoacrylate by any well known conventional technique.

In another embodiment the bioabsorbable composition is a copolymer including epsilon-caprolactone and lactide.

Suitable caprolactone/lactide copolymers include random copolymers containing about 40 to about 90 percent by weight epsilon-caprolactone and about 60 to about 10 percent by weight lactide. Such polymers can be synthesized using well known techniques such those described in Principles of Polymerization, George Odian, III Edition; 1991 pp. 569–573, the contents of which are incorporated herein by reference.

It is further contemplated that one or more medico-surgically useful substances can be incorporated into the presently disclosed blends, e.g., those medico-surgically useful substances which accelerate or beneficially modify the healing process when particles are applied to a surgical repair site. So, for example, the tissue adhesive can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the tissue adhesives, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

In order that those skilled in the art may be better able to practice the compositions and methods described herein, the following examples are given as an illustration of the preparation of blends herein. It should be noted that the invention is not limited to the specific details embodied in the examples.

EXAMPLE 1

Dry glycolide (222 grams) and distilled epsilon-caprolactone (2000 grams), were added to a reactor along with 0.44 grams of distilled stannous octoate and 2.2 grams of mannitol. The mixture was dried for about 6 hours with agitation under flow of nitrogen. The reactor temperature was then set at 160° C. and polymerization was conducted with stirring under a nitrogen atmosphere for about 20 hours.

The reaction product was then isolated, comminuted, and treated to remove residual reactants using known techniques. The treatment to remove residual reactants occurred at 90° C. for 48 hours under vacuum.

EXAMPLE 2

About 200 milligrams of the copolymer of Example 1 were added to a vial containing about 1 milliliter of n-butyl cyanoacrylate. The vial was then shaken for about 10 hours. The reaction product was then sampled.

EXAMPLE 3

About 200 milligrams of the copolymer of Example 1 were added to a vial containing about 1 milliliter of octyl cyanoacrylate. The vial was then shaken for about 10 hours. The reaction product was then sampled.

EXAMPLE 4

Epsilon-caprolactone (20 grams) and lactide (20 grams) were added to a reactor along with 0.008 grams of Stannous Octoate and 0.06 grams mannitol. The mixture was heated and placed in an oven at 165° C. for about 48 hours with stirring.

The reaction product was then isolated and treated to remove residual reactants using known techniques. The treatment to remove residual reactants occurred at 90° C. for 45 hours under vacuum.

EXAMPLE 5

About 125 milligrams of the copolymer of Example 4 were added to a vial containing about 1 milliliter of n-butyl cyanoacrylate. The vial was then shaken for about 5 minutes. The reaction product was then sampled.

EXAMPLE 6

Epsilon-caprolactone (28 grams) and glycolide (12 grams) were added to a polymerization tube along with 0.008 grams of Stannous Octoate and 0.105 grams diethylene glycol. The mixture was heated and placed at 165° C. for about 24 hours with stirring.

The reaction product was then isolated and treated to remove residual reactants using known techniques. The treatment to remove residual reactants occurred at 90° C. for 48 hours under vacuum.

EXAMPLE 8

About 125 milligrams of the copolymer of Example 7 were added to a vial containing about 875 milligrams of n-butyl cyanoacrylate. The vial was then shaken for about 10 hours. The reaction product was the sampled.

EXAMPLE 9

About 32 grams of trimethylene carbonate and about 8 grams glycolide were added to a polymerization tube along with 0.008 grams stannous chloride and about 0.06 grams of mannitol. The mixture was heated and placed in an oven at 165° C. for 48 hours.

The reaction product was then isolated and treated to remove residual reactants using known techniques. The treatment to remove residual reactants occurred at 90° C. for 48 hours under vacuum.

EXAMPLE 10

About 125 milligrams of the copolymer of Example 7 were added to a vial containing about 875 milligrams of n-butyl cyanoacrylate. The vial was then shaken for about 10 hours. The reaction product was the sampled.

It will be understood that various modifications may be made to the embodiments disclosed herein. For example, the compositions disclosed herein may be blended with other biocompatible, bioabsorbable, or nonbioabsorbable materials. Therefore, the above description should not be construed as limiting, but merely as exemplifications of preferred embodiments. Those skilled in the art will envision other modifiocations within the scope and spirit of the claims appended hereto.

What is claimed is:

1. A blend comprising at least one bioabsorbable component and an octyl cyanoacrylate wherein the bioabsorbable component contains a copolymer having from about 80% to about 95% by weight caprolactone and a material selected from the group consisting of glycolide, trimethylene carbonate, dioxanone, alkylene glycols, esteramides, and combinations thereof.

2. The blend of claim 1 wherein the bioabsorbable component comprise about 40 weight percent to about 95 weight percent of the blend.

3. The blend of claim 1 wherein the bioabsorbable component comprise about 5 weight percent to about 60 weight percent of the blend.

4. The blend of claim 1 wherein the bioabsorbable component comprise about 10 weight percent to about 60 weight percent of the blend.

5. The blend of claim 1 wherein the bioabsorbable component comprise about 12 weight percent to about 20 weight percent of the blend.

6. The blend of claim 1 wherein the cyanoacrylate component comprises about 40 weight percent to about 95 weight percent of the blend.

7. The blend of claim 1 wherein the cyanoacrylate component comprises about 60 weight percent to about 90 weight percent of the blend.

8. The blend of claim 1 wherein the cyanoacrylate component comprises about 80 weight percent to about 88 weight percent of the blend.

* * * * *